(12) United States Patent
Hosaka

(10) Patent No.: US 11,628,430 B2
(45) Date of Patent: Apr. 18, 2023

(54) METHOD FOR MANUFACTURING CATALYST LIQUID

(71) Applicant: KURARAY CO., LTD., Kurashiki (JP)

(72) Inventor: Yusaku Hosaka, Kamisu (JP)

(73) Assignee: KURARAY CO., LTD., Okayama (JP)

( * ) Notice: Subject to any disclaimer, the term of this patent is extended or adjusted under 35 U.S.C. 154(b) by 479 days.

(21) Appl. No.: 16/480,082

(22) PCT Filed: Feb. 21, 2018

(86) PCT No.: PCT/JP2018/006132
§ 371 (c)(1),
(2) Date: Jul. 23, 2019

(87) PCT Pub. No.: WO2018/155473
PCT Pub. Date: Aug. 30, 2018

(65) Prior Publication Data
US 2019/0381489 A1    Dec. 19, 2019

(30) Foreign Application Priority Data

Feb. 27, 2017  (JP) .............................. JP2017-034584

(51) Int. Cl.
| | | |
|---|---|---|
| B01J 31/24 | (2006.01) | |
| B01J 31/22 | (2006.01) | |
| B01J 37/04 | (2006.01) | |
| C07C 27/10 | (2006.01) | |
| C07F 9/50 | (2006.01) | |

(52) U.S. Cl.
CPC ....... B01J 31/2404 (2013.01); B01J 31/2282 (2013.01); B01J 37/04 (2013.01); C07C 27/10 (2013.01); C07F 9/5022 (2013.01); *B01J 2231/20* (2013.01); *B01J 2531/824* (2013.01)

(58) Field of Classification Search
None
See application file for complete search history.

(56) References Cited

U.S. PATENT DOCUMENTS

| | | |
|---|---|---|
| 4,642,392 A | 2/1987 | Hanes |
| 2004/0059170 A1 | 3/2004 | Rottger et al. |
| 2005/0240039 A1 | 10/2005 | Rottger et al. |
| 2012/0046475 A1 | 2/2012 | Leeuwen et al. |

FOREIGN PATENT DOCUMENTS

| | | |
|---|---|---|
| CN | 101835786 | 9/2010 |
| EP | 0 296 550 | 12/1988 |
| EP | 1 249 455 | 10/2002 |
| JP | 64-85988 A | 3/1989 |
| JP | 2002-371088 A | 12/2002 |
| JP | 2002-371089 | 12/2002 |
| JP | 2005-536482 A | 12/2005 |
| JP | 2006-327960 A | 12/2006 |
| JP | 2010-215604 A | 9/2010 |
| JP | 2010-248099 A | 11/2010 |
| JP | 2012-526780 A | 11/2012 |
| WO | 2016/164258 | 10/2016 |

OTHER PUBLICATIONS

Extended European Search Report issued in EP Patent Application No. 18757923.0, dated Jan. 12, 2021.
International Search Report dated Apr. 10, 2018 in PCT/JP2018/006132 filed on Feb. 21, 2018.
Catalysis Society of Japan, "Catalysts Lecture, vol. 4 (Basic Edition 4), Reaction Mechanism Determination Methods for Complex Catalysts (1st Ed.)," Kodansha Ltd., Jun. 1986, pp. 162-172 (total 18 pages).
Crabtree, R. H., "Deactivation in Homogeneous Transition Metal Catalysis: Causes, Avoidance, and Cure," Chemical Reviews, ACS Publications, American Chemical Society, Chem. Rev., 2015, vol. 115, pp. 127-150.

*Primary Examiner* — Yun Qian
(74) *Attorney, Agent, or Firm* — Greenblum & Bernstein, P.L.C.

(57) ABSTRACT

There is provided a method for producing a catalyst liquid containing a Group 6 to 11 transition metal catalyst in which the transition metal catalyst can be prevented from being blackened during storage, the method including performing addition of an alkenyl compound and addition of a phosphorus ligand, and then performing addition of a Group 6 to 11 transition metal catalyst

3 Claims, 1 Drawing Sheet

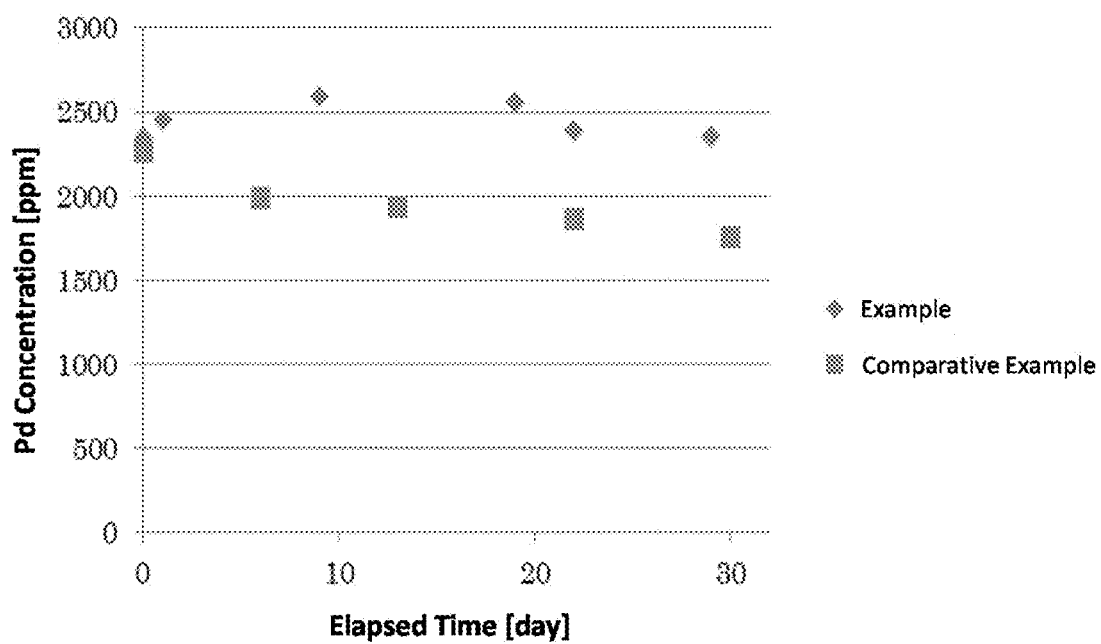

METHOD FOR MANUFACTURING CATALYST LIQUID

TECHNICAL FIELD

The present invention relates to a method for producing a catalyst liquid.

BACKGROUND ART

As described in NPLs 1 to 2, a transition metal complex catalyst to be used in a liquid-phase homogeneous system has high reaction selectivity but is, on the other hand, difficult to use industrially. One reason is, for example, because of low thermal/chemical stability of a transition metal catalyst. For compensation for it, in an industrial process, some devising will be necessary not only for reaction conditions but also for modes of catalyst introduction into a reaction system.

For example, in PTLs 1 and 2, in a telomerization reaction between a conjugated diene and an active hydrogen compound, a transition metal catalyst is not added directly to the reaction system, but a catalyst liquid is preliminarily prepared by mixing a transition metal catalyst and a ligand with a solvent and is then added to a reaction system. This is a procedure for preventing reduction in reactivity and for preventing generation of unintended impurities. Specifically, PTL 1 says that, for solving the problem that a phosphorus ligand such as a trisubstituted phosphine to be used for stabilizing a palladium catalyst of a transition metal catalyst may lower the reaction activity, the phosphorus ligand is preliminarily converted into a phosphonium salt thereof and is added to a reaction system.

CITATION LIST

Patent Literature

PTL 1: JP 64-085988 A
PTL 2: JP 2002-371088 A

Non-Patent Literature

NPL 1: Catalysis Society of Japan, "Catalysts Lecture, Vol. 4 (Basic Edition 4), Reaction Mechanism Determination Methods for Complex Catalysts (1st Ed.)", Kodansha Ltd., June 1986, pp. 162-172
NPL 2: Chemical Reviews (Chem. Rev.), 2015, Vol. 115, pp. 127-150

SUMMARY OF INVENTION

Technical Problem

However, when the present inventor prepared a large quantity of the catalyst liquid described in PTLs 1 and 2 all at a time, then used a part thereof for continuous reaction, while storing the remaining part thereof, and adequately added a necessary amount of the liquid to the reaction system for compensating for the catalyst having been lost through elution in the process of the continuous reaction, then the present inventor found that, in the stored catalyst liquid, the transition metal catalyst became blackened with time (owing to the phenomenon that the transition metal catalyst is reduced to precipitate as a metal thereof). In addition, in the case where a large quantity of the catalyst liquid was prepared all at a time, there occurred a problem of productivity that, depending on the solubility of the transition metal catalyst and the ligand, it took 2 days or more for the preparation in some cases.

Specifically, an object of the present invention is to provide a method for producing a catalyst liquid capable of preventing the transition metal catalyst in the catalyst liquid during storage from being blackened.

Solution to Problem

As a result of assiduous studies, the present inventor has found that, in production of a catalyst liquid, when a Group 6 to 11 transition metal catalyst is added after addition of an alkenyl compound and a phosphorus ligand, the transition metal catalyst can be prevented from being blackened during storage of the catalyst liquid, and based on this finding, the present inventor has made further investigations and have completed the present invention.

The present invention relates to the following [1] to [12].
[1] A method for producing a catalyst liquid, including performing addition of an alkenyl compound and addition of a phosphorus ligand, and then performing addition of a Group 6 to 11 transition metal catalyst.
[2] The production method according to [1], wherein the alkenyl compound, the phosphorus ligand, and the Group 6 to 11 transition metal catalyst are added in that order.
[3] The production method according to [1] or [2], wherein the alkenyl compound is an allyl alcohol compound.
[4] The production method according to [3], wherein the allyl alcohol compound is an alkadienol compound having 8 to 12 carbon atoms.
[5] The production method according to [4], wherein the alkadienol compound having 8 to 12 carbon atoms is 2,7-octadien-1-ol.
[6] The production method according to any of [1] to [5], wherein the phosphorus ligand is a tertiary phosphorus compound.
[7] The production method according to [6], wherein the tertiary phosphorus compound is a hydrophobic aromatic phosphine or a hydrophilic aromatic phosphine.
[8] The production method according to [6], wherein the tertiary phosphorus compound is a hydrophilic aromatic phosphine.
[9] The production method according to [6], wherein the tertiary phosphorus compound is lithium 3-(diphenylphosphino)benzenesulfonate or triethylamine 3-(diphenylphosphino)benzenesulfonate.
[10] The production method according to any of [1] to [9], wherein the Group 6 to 11 transition metal catalyst is a palladium compound.
[11] The production method according to any of [1] to [10], wherein the catalyst liquid is a catalyst liquid for a telomerization reaction.
[12] The production method according to [11], wherein the telomerization reaction is a telomerization reaction using butadiene or isoprene as a raw material.

Advantageous Effects of Invention

According to the production method of the present invention, the transition metal catalyst can be prevented from being blackened during storage of the catalyst liquid containing a Group 6 to 11 transition metal catalyst.

BRIEF DESCRIPTION OF DRAWING

FIG. 1 plots a change of palladium concentration (in terms of palladium acetate) relative to the elapsed days in the catalyst liquids produced in Example and Comparative Example.

DESCRIPTION OF EMBODIMENTS

Hereinunder the present invention is described in detail.

The present invention relates to a method for producing a catalyst liquid containing a Group 6 to 11 transition metal catalyst (hereinafter this may be simply referred to as "the production method of the present invention"). In the production method for a catalyst liquid of the present invention, a Group 6 to 11 transition metal catalyst is added after addition of an alkenyl compound and addition of a phosphorus ligand. According to the production method, in the catalyst liquid containing a Group 6 to 11 transition metal catalyst, the transition metal catalyst can be prevented from being blackened during storage. Though not always clear, the reason why the transition metal catalyst can be prevented from being blackened when the components are added in the order mentioned above is considered to be because, by adding the components in that order, an unstable complex of a Group 6 to 11 transition metal catalyst and a phosphorus ligand alone can be prevented from being formed, and formation of a stable π-allyl complex of an alkenyl compound, a phosphorus ligand and a Group 6 to 11 transition metal catalyst or a phosphonium salt of an alkenyl compound and a phosphorus ligand can finish early.

An alkenyl compound and a phosphorus ligand may be added simultaneously or sequentially. In the production method for a catalyst liquid of the present invention, from the viewpoint of increasing the solubility of the phosphorus ligand and the Group 6 to 11 transition metal catalyst to shorten the time for preparing the catalyst liquid, preferably the alkenyl compound, the phosphorus ligand and the Group 6 to 11 transition metal catalyst are added in that order.

In this description, the "alkenyl compound" is a compound having at least one, carbon-carbon unsaturated double bond in the molecule. The "Group 6 to 11 transition metal" of the "group 6 to 11 transition metal catalyst" is a transition metal of Groups 6 to 11 in the long-form periodic table.

<Alkenyl Compound>

The alkenyl compound for use in the present invention is preferably a compound capable of reacting with a phosphorus ligand and a Group 6 to 11 transition metal catalyst to form a stable complex and capable of forming a phosphonium salt through reaction with a phosphorus ligand.

From the above-mentioned viewpoints and from the viewpoint of solubility in a solvent to be mentioned below, the alkenyl compound for use in the present invention is preferably an allyl alcohol compound or a derivative thereof, and more preferably an allyl alcohol compound. The "allyl alcohol compound" includes allyl alcohol and an alcohol resulting from substitution of at least one hydrogen in the allyl group moiety of allyl alcohol. The "derivative of an allyl alcohol compound" is an alcohol derivative resulting from substitution of the hydrogen atom of the hydroxy group in the allyl alcohol compound, and includes an ester compound and an ether compound of an allyl alcohol compound. The derivative is preferably an ester compound.

The allyl alcohol compound or a derivative thereof favorably used as the alkenyl compound in the present invention is more preferably a compound represented by the following general formula (I).

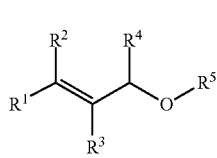

In the general formula (I), $R^1$ to $R^4$ each independently represent a hydrogen atom, or a hydrocarbon group having 1 to 12 carbon atoms. $R^5$ represents a hydrogen atom, a hydrocarbon group having 1 to 12 carbon atoms, or a group represented by —CO—$R^6$ or —$SO_2$—$R^6$ where $R^6$ represents a hydrocarbon group having 1 to 12 carbon atoms.

The hydrocarbon group for $R^1$ to $R^4$ is preferably a chain-like aliphatic group. The chain-like aliphatic group may be linear or branched, but is preferably a linear aliphatic group. The aliphatic group may be a saturated aliphatic group or an unsaturated aliphatic group. The hydrocarbon group for $R^1$ to $R^4$ preferably has 1 to 8 carbon atoms, more preferably 1 to 6 carbon atoms.

The hydrocarbon group for $R^5$ is preferably a chain-like aliphatic group. The chain-like aliphatic group may be linear or branched, but is preferably a linear aliphatic group. The aliphatic group may be a saturated aliphatic group or an unsaturated aliphatic group, but is preferably a saturated aliphatic group. The hydrocarbon group for $R^5$ preferably has 1 to 8 carbon atoms, more preferably 1 to 5 carbon atoms, and even more preferably 1 to 3 carbon atoms.

$R^5$ is preferably a hydrogen atom or a group represented by —CO—$R^6$, and is more preferably a hydrogen atom.

$R^6$ represents a hydrocarbon group having 1 to 12 carbon atoms, and is preferably a chain-like aliphatic group. The chain-like aliphatic group may be linear or branched, but is preferably a linear aliphatic group. The aliphatic group may be a saturated aliphatic group or an unsaturated aliphatic group, but is preferably a saturated aliphatic group. The hydrocarbon group for $R^6$ preferably has 1 to 8 carbon atoms, more preferably 1 to 5 carbon atoms, and even more preferably 1 to 3 carbon atoms.

The carbon number of the alkenyl compound for use in the present invention is, from the viewpoint of complex formation capability, phosphonium salt formation capability and solubility in a solvent to be mentioned below, preferably 3 to 24, more preferably 6 to 18, and even more preferably 8 to 12.

More specifically, examples of the alkenyl compound for use in the present invention include allyl alcohol compounds such as allyl alcohol (2-propen-1-ol), 2-methyl-2-prop en-1-ol, 2-buten-1-ol, 2,5-hexadien-1-ol, 2,7-octadien-1-ol, 1,4-pentadien-3-ol, 1,7-octadien-3-ol and 2-octen-1-ol; and allyl alcohol esters such as allyl acetate, 2-methyl-2-propenyl acetate, 2,5-hexadienyl acetate, 2,7-octadienyl acetate, 1-vinyl-5-hexenyl acetate, 1-vinyl-2-propenyl propionate, and 2-octenyl propionate.

Among these, allyl alcohol compounds are preferred.

Among the allyl alcohol compounds, alkadienol compounds having 8 to 12 carbon atoms, such as 2,7-octadien-1-ol and 1,7-octadien-3-ol are preferred, and 2,7-octadien-1-ol is more preferred.

One alone of these may be used, or two or more kinds thereof may be used in combination.

<Phosphorus Ligand>

The phosphorus ligand for use in the present invention is preferably a compound containing a phosphorus atom and capable of coordinating with a Group 6 to 11 transition metal to form a complex. The phosphorus ligand is preferably a tertiary phosphorus compound such as phosphine, phosphite or phosphonite.

Examples of the tertiary phosphorus compound include an aliphatic phosphine such as triisopropyl phosphine, a tri-n-butyl phosphine, and tri-n-octyl phosphine; an alicyclic phosphine such as tricyclohexyl phosphine; a hydrophobic aromatic phosphine such as triphenyl phosphine, tritolyl phosphine, diphenyl-p-chlorophenyl phosphine and trimesityl phosphine; an aliphatic aromatic phosphine such as lithium 3-(diphenylphosphino)benzenesulfonate, sodium 3-(diphenylphosphino)benzenesulfonate, triethylamine 3-(diphenylphosphino)benzenesulfonate, and tris(sodium 3-sulfophenyl) phosphine; a phosphite such as triethyl phosphite, tributyl phosphite, and triisopropyl phosphite; and a phosphonite such as octyldioctoxy phosphine, and butyldibutoxy phosphine.

Among these, an aromatic phosphine, that is, a hydrophobic aromatic phosphine or a hydrophilic aromatic phosphine is preferred, an aliphatic aromatic phosphine is more preferred, and lithium 3-(diphenylphosphino)benzenesulfonate or triethylamine 3-(diphenylphosphino)benzenesulfonate is especially preferred.

One alone of these may be used, or two or more kinds thereof may be used in combination.

The aliphatic aromatic phosphine is an aromatic phosphine having a hydrophilic group, such as a group represented by —$SO_3M$, —COOM (where M represents an alkali metal ion or —$H^+N(R^{11})(R^{12})(R^{13})$ or —$N(R^{14})(R^{15})$. $R^{11}$, $R^{12}$ and $R^{13}$ each independently represent a hydrogen atom or an alkyl group having 1 to 3 carbon atoms, and $R^{14}$ and $R^{15}$ each independently represent an alkyl group having 1 to 3 carbon atoms.

The hydrophobic aromatic phosphine is an aromatic phosphine not having the above-mentioned hydrophilic group.

<Group 6 to 11 Transition Metal Catalyst>

The Group 6 to 11 transition metal catalyst for use in the present invention may be a compound having a Group 6 to 11 transition metal in the long-form periodic table.

The transition metal in the Group 6 to 11 transition metal catalyst is preferably at least one selected from the group of a Group 6 transition metal and a Group 10 transition metal, more preferably a Group 10 transition metal, and even more preferably palladium.

More specifically, examples of the Group 6 to 11 transition metal catalyst include a molybdenum compound, a tungsten compound, a nickel compound, a palladium compound and a platinum compound. Among these, a palladium compound is preferred.

Examples of the palladium compound include a divalent palladium complex such as palladium acetate, palladium acetylacetonate, palladium chloride and palladium nitrate; and a 0-valent palladium complex such as tris(dibenzylideneacetone) dipalladium, tetrakis(triphenylphosphine) palladium, and bis(1,5-cyclooctadiene) palladium.

Among these, one or more selected from the group consisting of palladium acetate, palladium chloride and tris(dibenzylideneacetone) dipalladium are preferred, and palladium acetate is more preferred.

One alone of these may be used, or two or more kinds thereof may be used in combination.

(Solvent)

In the present invention, for more smoothly carrying out the production of the catalyst liquid, preferably, a solvent is used.

Not specifically limited, the solvent is preferably one capable of at least partly dissolving the alkenyl compound, the phosphorus ligand and the Group 6 to 11 transition metal catalyst.

Examples of such solvents include ethers such as diethyl ether, tetrahydrofuran and 1,4-dioxane; ketones such as acetone, and methyl ethyl ketone; nitriles such as acetonitrile and benzonitrile; sulfones such as sulfolane and methylsulfolane; esters such as methyl acetate and ethyl acetate; aromatic hydrocarbons such as benzene, toluene and xylene; and aliphatic hydrocarbons such as butane, hexane and cyclohexane.

Among these, tetrahydrofuran, 1,4-dioxane or sulfolane is preferred, and sulfolane is more preferred.

One alone of these may be used, or two or more kinds thereof may be used in combination. A solvent and water may be used in combination.

In the present invention, the amount of the alkenyl compound, the phosphorus ligand, the Group 6 to 11 transition metal catalyst and the optional component, solvent is not specifically limited, and may be appropriately controlled in accordance with the use of the catalyst liquid.

For example, the amount of the alkenyl compound to be used in the production method of the present invention is preferably 0.1 to 100 mol relative to 1 mol of the transition metal in the Group 6 to 11 transition metal catalyst, more preferably 1 to 50 mol, and the amount of the phosphorus ligand to be used is preferably 0.1 to 100 mol relative to 1 mol of the transition metal in the Group 6 to 11 transition metal catalyst, more preferably 1 to 50 mol.

In the case where a solvent is used, the amount thereof to be used is generally within a range of 1 to 99.5% by mass relative to the total amount of the catalyst liquid.

The concentration of the catalyst liquid to be obtained is, as the concentration of the transition metal in the Group 6 to 11 transition metal catalyst, generally within a range of 0.1 to 10,000 ppm, preferably 50 to 5,000 ppm, more preferably 100 to 3,000 ppm.

The production method for the catalyst liquid of the present invention may be carried out, for example, according to the following procedure.

First, an alkenyl compound, a phosphorus ligand and optionally a solvent are added to a reactor and mixed by stirring therein. As described above, an alkenyl compound and a phosphorus ligand may be added simultaneously or successively. From the viewpoint of increasing the solubility of a phosphorus ligand and a Group 6 to 11 transition metal catalyst to shorten the preparation time for the catalyst liquid, preferably, an alkenyl compound and a phosphorus ligand are added in that order. For example, in the case of using a solvent, an alkenyl compound and the solvent may be added first so as to dissolve the alkenyl compound, and then a phosphorus compound may be added to and mixed therein.

Next, an alkenyl compound, a phosphorus ligand and optionally a solvent are added to give a mixture, and then a Group 6 to 11 transition metal catalyst is added to the resultant mixture, and mixed with stirring until the cloudiness disappears to give a catalyst liquid.

Preferably, the above operation is carried out in an inert gas atmosphere such as nitrogen. The temperature in adding and mixing the components is not specifically limited, and, in general, the operation may be carried out at a temperature of 5 to 50° C.

The use of the catalyst liquid produced according to the production method of the present invention is not specifically limited, and for example, the catalyst liquid may be used as a catalyst liquid for a telomerization reaction, or a catalyst liquid for a Tsuji-Trost reaction.

Above all, the production method of the present invention is favorably employed in the case where the intended catalyst liquid is a catalyst liquid for a telomerization reaction, and is more favorably employed in the case where the intended catalyst liquid is a catalyst liquid for a telomerization reaction using butadiene or isoprene (especially 1,3-butadiene or 2-methyl-1,3-butadiene) as the raw material.

EXAMPLES

Hereinunder the present invention is described in more detail by Example, but the present invention is not whatsoever limited by the Example. Unless otherwise specifically indicated, the operation was carried out in a nitrogen atmosphere.

Example 27.29 g (27.29 mL) of distilled water and 28.69 g (22.77 mL) of sulfolane were put into a glass-made three-neck flask equipped with a magnetic stirrer, and then 0.676 g (0.777 mL) of 2,7-octadien-1-ol was added to and dissolved therein. Next, 1.0819 g (2.44 mmol) of triethylamine 3-(diphenylphosphino)benzenesulfonate was added and finally 0.1354 g (0.603 mmol) of palladium acetate was added thereto and stirred at room temperature for 10 minutes. The resultant catalyst liquid was transferred into a Hiper glass cylinder (manufactured by Taiatsu Techno Corporation, material: Hyper glass), and stored in a carbon dioxide 0.5 MPa atmosphere at room temperature.

During storage, the catalyst liquid was adequately sampled, and the palladium concentration (in terms of palladium acetate) therein was measured using an atomic absorption spectrophotometer (manufactured by Hitachi High-Tech Science Corporation, "Z-5010"). The change of the palladium concentration (ppm) relative to the elapsed days is shown in Table 1.

Comparative Example 27.30 g (27.30 mL) of distilled water and 28.76 g (22.82 mL) of sulfolane were put into a glass-made three-neck flask equipped with a magnetic stirrer, and then 1.0715 g (2.42 mmol) of triethylamine 3-(diphenylphosphino)benzenesulfonate was dissolved therein. The colorless solution was transferred into a Hyper glass cylinder, and left in a carbon dioxide 0.5 MPa atmosphere at room temperature for 1 hour. After thus left, this was depressurized, and a part thereof was drawn away through a syringe and transferred into a flask. 0.1387 g (0.618 mmol) of palladium acetate was added thereto, and well stirred to be homogenized, then returned back to the Hyper glass cylinder, and the contents were well stirred by drawing out and returning back through a syringe and by shaking of the container. Subsequently, this was again left in a carbon dioxide 0.5 MPa atmosphere for 16 hours. After the disappearance of the cloudiness of the liquid was confirmed, this was depressurized, and 0.634 g (0.728 mL) of 2,7-octadien-1-ol was added thereto. The resultant catalyst liquid was stored in a carbon dioxide 0.5 MPa atmosphere at room temperature.

During storage, the catalyst liquid was adequately sampled, and the palladium concentration (in terms of palladium acetate) therein was measured using an atomic absorption spectrophotometer (manufactured by Hitachi High-Tech Science Corporation, "Z-5010"). The change of the palladium concentration (ppm) relative to the elapsed days is shown in Table 1.

TABLE 1

| | Elapsed Days | | | | | | | | |
| --- | --- | --- | --- | --- | --- | --- | --- | --- | --- |
| | 0 | 1 | 6 | 9 | 13 | 19 | 22 | 29 | 30 |
| Example | 2340 | 2450 | 2590 | | 2560 | 2390 | 2350 | | |
| Comparative Example | 2260 | | 1990 | | 1930 | | 1860 | | 1760 |

(On day 0, the value was calculated from the amount of the chemical liquid.)

In Example where the alkenyl compound and the phosphorus ligand were first added in the absence of the Group 6 to 11 transition metal catalyst, and then the Group 6 to 11 transition metal catalyst, palladium acetate was added thereto, there was no significant change in the palladium concentration in accordance with the elapsed days, which suggests that blackening was suppressed. On the other hand, in Comparative Example where the phosphorus ligand, the Group 6 to 11 transition metal catalyst and the alkenyl compound were added in that order, the palladium concentration in the catalyst liquid decreased in accordance with the elapsed days, which suggests occurrence of blackening.

In addition, in Example, the catalyst liquid preparation finished in a short period of time, but in Comparative Example, much time was taken for dissolving the components, and the preparation time was prolonged.

INDUSTRIAL APPLICABILITY

The production method of the present invention is advantageous in that, in producing a catalyst liquid containing a Group 6 to 11 transition metal catalyst, an industrial-scale amount of a catalyst liquid can be prepared with good storability.

The invention claimed is:
1. A method for producing a catalyst liquid, comprising performing addition of an alkenyl compound and a phosphorus ligand to a solvent, then
performing addition of a Group 6 to 11 transition metal catalyst, and then
stirring at room temperature, wherein the alkenyl compound, the phosphorus ligand, and the Group 6 to 11 transition metal catalyst are added in that order;
the alkenyl compound is 2,7-octadien-1-ol;
the phosphorus ligand is triethylamine 3-(diphenylphosphino)benzenesulfonate;
the Group 6 to 11 transition metal catalyst is palladium acetate; and the solvent is at least one selected from sulfolane and water.

2. The production method according to claim 1, wherein the catalyst liquid is a catalyst liquid for a telomerization reaction.

3. The production method according to claim 2, wherein the telomerization reaction is a telomerization reaction using butadiene or isoprene as a raw material.

* * * * *